(12) United States Patent
Bartholomaeus et al.

(10) Patent No.: US 8,133,510 B2
(45) Date of Patent: Mar. 13, 2012

US008133510B2

(54) FORM OF ADMINISTRATION BASED ON CROSSLINKED HYDROPHILIC POLYMERS

(75) Inventors: Johannes Bartholomaeus, Aachen (DE); Maria Cristina Vázquez Lantes, Munich (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1108 days.

(21) Appl. No.: 10/596,202

(22) PCT Filed: Dec. 13, 2004

(86) PCT No.: PCT/EP2004/014147
§ 371 (c)(1),
(2), (4) Date: Jun. 2, 2006

(87) PCT Pub. No.: WO2005/056648
PCT Pub. Date: Jun. 23, 2005

(65) Prior Publication Data
US 2008/0286342 A1    Nov. 20, 2008

(30) Foreign Application Priority Data
Dec. 12, 2003  (DE) ................................ 103 58 748

(51) Int. Cl.
*C01B 7/01*    (2006.01)
(52) U.S. Cl. .......... 424/487; 427/213; 427/214; 424/44
(58) Field of Classification Search ............... 424/464, 424/458, 487; 427/213, 214, 495
See application file for complete search history.

(56) References Cited

U.S. PATENT DOCUMENTS

| | | | |
|---|---|---|---|
| 4,777,046 A * | 10/1988 | Iwakura et al. ............... 424/435 |
| 6,245,351 B1 * | 6/2001 | Nara et al. .................... 424/461 |
| 6,375,963 B1 | 4/2002 | Repka et al. |
| 6,780,504 B2 | 8/2004 | Rupprecht et al. |
| 6,800,329 B2 * | 10/2004 | Horstmann et al. .......... 427/379 |

FOREIGN PATENT DOCUMENTS

| | | |
|---|---|---|
| DE | 199 32 603 A1 | 1/2001 |
| DE | 10146251    * | 4/2003 |
| DE | 101 46 251 A1 | 8/2003 |
| EP | 0 410 696 A1 | 1/1991 |
| WO | WO/99/08691 | 2/1999 |
| WO | WO 99/55312 | 11/1999 |
| WO | WO 01/58430 A1 | 8/2001 |
| WO | WO 03/063839 A1 | 8/2003 |

* cited by examiner

*Primary Examiner* — Fereydoun G Sajjadi
*Assistant Examiner* — Danielle Sullivan
(74) *Attorney, Agent, or Firm* — Frommer Lawrence & Haug LLP

(57) ABSTRACT

The invention relates to a film-shaped form of administration for topically administering at least one agent and/or nutrient to a living being. Said form of administration comprises at least one agent-containing and/or nutrient-containing layer that is based on crosslinked hydrophilic polymers which are crosslinked with at least one polyacrylic acid derivative.

12 Claims, No Drawings

FORM OF ADMINISTRATION BASED ON CROSSLINKED HYDROPHILIC POLYMERS

The present invention relates to a dosage form in film form for surface administration of at least one active ingredient and/or nutrient to a living creature comprising at least one active ingredient-containing and/or nutrient-containing layer based on hydrophilic polymers which have been crosslinked with at least one polyacrylic acid derivative.

Dosage forms in film form for surface administration normally have a multilayer structure and typically consist of a covering layer, of an active ingredient-containing and/or nutrient-containing layer and an adhesive layer.

The published application DE 199 32 603 has disclosed the crosslinking of hydrophilic polymers with tannin to produce dosage forms in film form for administering active ingredients and/or nutrients. The use of tannin may confer on the dosage form both a yellowish color and an unpleasant taste.

The object therefore was to provide a dosage form in film form based on crosslinked hydrophilic polymers where the crosslinker used causes no disadvantageous change in the dosage form.

This object has been achieved by the provision of the inventive dosage form in film form for surface administration of at least one active ingredient and/or nutrient to a living creature comprising at least one active ingredient-containing and/or nutrient-containing layer based on crosslinked hydrophilic polymers, which is characterized in that the hydrophilic polymers have been crosslinked with at least one polyacrylic acid derivative.

Suitable as polyacrylic acid derivative for the crosslinking of hydrophilic polymers are without restriction all pharmaceutically acceptable polyacrylic acid derivatives such as, for example, an optionally crosslinked polyacrylic acid, preferably a polyacrylic acid crosslinked with allylsucrose or allylpentaerythritol (carbomer according to USP-NF) and/or a polyacrylic acid crosslinked with divinylglycol, where appropriate neutralized with calcium (polycarbophil according to USP-NF). A polyacrylic acid crosslinked with divinylglycol is particularly preferred.

Hydrophilic polymers suitable for the inventive dosage form in film form are in particular water-soluble cellulose ethers, preferably hydroxypropylmethylcellulose, hydroxyethylcellulose and/or methyl-cellulose, particularly preferably hydroxypropylmethyl-cellulose.

The use of polyacrylic acid derivatives results in dosage forms whose mechanical properties are comparable with those of dosage forms with tannin as crosslinker.

Thus, the crosslinking of the film-forming hydrophilic polymers with polyacrylic acid derivatives ensures adequately secure handling of the dosage form in film form, e.g. on removal from the package and introduction on the site of application, without damaging the dosage form by tearing, and prevents rapid dissolution of the dosage form at the site of application, e.g. on a wet mucous membrane.

The inventive dosage form in film form is employed for surface administration of at least one active ingredient and/or nutrient to a living creature.

There is in principle no restriction on the active ingredients and/or nutrients contained in the active ingredient-containing and/or nutrient-containing layer. The active ingredients or nutrients are, however, preferably fragrances, flavorings, diagnostic aids, crop protection agents, active pharmaceutical ingredients, vitamins, fertilizers and/or other nutrients.

Active pharmaceutical ingredients which can be used are analgesics, antiallergics, antibiotics, antiemetics, antiseptics, antihistamines, antihypertensives, appetite suppressants, cardiac remedies, chemo-therapeutic agents, enzyme products, hormones, immuno-modulators, inoculations, local anesthetics, psychoactive drugs, spasmolytics, virustatics, vitamins and cytostatics.

Suitable active ingredients are in particular diamorphine, alfentanil, sufentanyl, pentazocine, buprenorphine, nefopam, flupirtine, tramadol, oxycodone, metamizole, propyphenanzone, phenazone, nifenazone, phenylbutazone, oxyphenbutazone, mofebutazone, diflunisal, meptazinol, methadone, pethidine, meloxicam, fenbufen, mefenamic acid, tenoxicam, azapropazone, piritramide, tramadol, amantadine, benzotropine, procyclidine, moclobemide, tranylcypromide, maprotiline, doxepin, opipramol, desipramine, imipramine, fluroxamine, paroxetine, trazodone, viloxazine, fluphenazine, perphenazine, promethazine, thioridazine, triflupromazine, prothipendyl, tiotixene, chlorprothixene, pipamperone, pimozide, fenethylline, trifluoperazine, thioridazine, oxazepam, alprazolam, clobazam, piracetam, melfalan, cyclophosphamide, trofosfamide, chlorambucil, lomustine, busilfan, prednimustine, mercaptopurine, thioguanine, hydroxycarbamide, altretamine, procarbazine, lisuride, methylsergide, pizotifen, roxatidine, pirenzipine, proglumide, bromopride, pheniramine, dimethindene, tritoqualine, loratadine, doxylamine, mequitazine, dexchlorpheniramine, triprolidine, oxatomide, moxonidine, doxazosine, urapidil, dihydralazine, deserpidine, alprenolol, bupranolol, penbutolol, esmolol, ciliprolol, metipranolol, nadolol, quinapril, fosinopril, cilazapril, democlocycline, lymecycline, oxytetracycline, sulfamethopyrazine, aerosoxacin, becampicillin, piperacillin, pivampicillin, cloxacillin, flucloxacillin, metronidazole, clindamycin, cefaclor, cefpodoxime, cephalexin, cefradine, pirbuterol, orciprenaline, clenbuterol, procaterol, choline theophyllinate, theophylline-ethylenediamine, Ketofen, viquidil, procainamide, mexiletine, tocainide, ipratropium, tobutamide, gliquidone, gliboruride, tolazamide, acarbose and pharmaceutically active salts or esters of the aforementioned active ingredients, and combinations of two or more of these active ingredients or salts or esters thereof.

Examples of suitable active ingredients are acebutolol, acetylcysteine, acetylsalicylic acid, aciclovir, albrazolam, alfacalcidol, allantoin, allopurinol, ambroxiol, amikacin, amiloride, aminoacetic acid, amiodarone, amitriptyline, amlodipine, amoxicillin, ampicillin, ascorbic acid, aspartame, astemizole, atenolol, beclometasone, benserazide, benzalkonium hydrochloride, benzocaine, benzoic acid, betametasone, bezafibrate, biotin, biperidene, bisoprolol, bromacepam, bromhexine, bromocriptine, budesonide, bufexamac, buflomedil, buspirone, caffeine, camphor, captopril, carbamacipine, carbidopa, carboplatin, cefachlor, cefalexin, cefadroxil, cefazolin, cefixime, cefotaxime, ceftazidine, ceftriaxone, cefuroxime, celedilin, chloramhenicol, chlorhexidine, chlorpheniramine, chlortalidone, choline, ciclosporin, cilastatin, cimetidine, ciprofloxacin, cisapride, cisplatin, clarithromycin, clavulanic acid, clomibramine, clonazepam, clonidine, clotrimazole, codeine, cholestyramine, cromoglicic acid, cyanocobalamin, cyproterone, desogetrel, dexamethasone, dexpanthenol, dexthromethorphan, dextropropoxiphen, diazepam, diclofenac, digoxin, dihydrocodeine, dihyderoergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradinol, etoposide, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentaminicin, Gingko Biloba, glibenclamide, glipizide, glozapine, Glycyrrhiza Glabra, griseofulvin, guaifenesin, haloperidol, heparin, hyaluronic acid, hydrochlorothiazide, hydrocodone, hydrocortisone, hydromorphone, ibratropium hydroxide, ibuprofen, imipenem, indomethacin, iohexol, iopamidol, isosorbide dinitrate, isosorbide mononitrate, isotretionin, ketotifen, ketoconazole, ketoprofen, ketorolac, labatalon, lactulose, lecithin, levocarnitine, levodopa, levoglutamide, levonorgestrel, levothyroxine, lidocaine, lipase, lipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamins and minerals, N-methylephedirne, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, phenoxifylline, phenoxymethyl-penicillin, phenylephrine, phenylpropanolamine, phenytoin, piroxicam, polymyxin B, povidone-iodine, pravastatin, prazepam, prazosin, prednisolone, prednisone, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamteren, trimethoprim, troxerutin, uracil, valproic acid, vancomycin, verapamil, vitamins E, zidovudine.

Further suitable active ingredients are prochlorperazine edisylal, iron-II sulfate, aminocaproic acid, potassium chloride, mecamylamine hydrochloride, procainamide hydrochloride, amphetamine sulfate, benzphetamine hydrochloride, isoporterenol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine maleate, anisindone, diphenadione, erythritol tetranitrate, dizoxin, isofurophate, acetazolamide, methazolamide, bendroflumethiazide, chlorpropamide, tolazamide, chlormadinone acetate, phenaglycodol, aluminum-aspirin, methotrexate, acetylsulfioxazole, progestins, estrogenic steroids, progestatinal steroids, corticosteroids, 17-β-estradiol, ethinylestradiol 3-methyl ester, hydrocortisone acetate, methyltesterone, 17-α-hydroxyprogesterone acetate, 19-norprogesterone, norethindrone, progesterone, norgesterone, norethynodrel and others.

Further examples of active ingredients are fenoprofen, sulindac, indoprofen, nitroglycerine, timolol, alprenolol, imipramine, chlorpromazine, dihydroxy-phenylalanine, pivaloxyloxyethyl ester of α-methyldopa hydrochloride, calcium gluconate, iron-II lactate, vincamine, phenoxybenzamine, blockers and the like. The active ingredients are disclosed in "Pharmaceutical Sciences" by Remingtom, 14th edition, 1979, Mack Publishing Co., Easton, Pa.; "The Drug, The Nurse, The Patient, Including Current Drug Handbook", 1974-1976, by Falconer et al, Saunder Co.,  Philadelphia, Pa., and "Medical Chemistry", 3rd edition, volume 1 and 2, by Burger, Wiley-Interscience, New York.

Representative medicaments which can be administered to warm-blooded animals, for example ruminants, with the aid of the inventive dosage form are inter alia anthelmintics such as mebendazole, levamisole, albendazole, cambendazole, fenbendazole, parbendazole, oxfendazole, oxybendazole, thiabendazole, tichlorofon, praziquantel, morantel and pirantel, and the like; antiparasitic agents such as avermectins and ivermectin as indicated in U.S. Pat. Nos. 4,199,569 and 4,389,397 (Merck) and in "Science", volume 221, pp. 823-828, 1983, where these ivermectin antiparasitic agents are indicated as suitable for helping to control worms normally occurring in mammals, such as roundworms (eel worms), long worms and the like, and also that ivermectin is suitable for the treatment of insect infections such as maggots, lice, mite mange and the like; antimicrobial agents such as chlorotetracycline, oxytetracycline, tetracycline, gentamicin, streptomycin, dihydro-streptomycin, bacitracins, erthromycin, ampicillins, penicillins, cephalosporins and the like; sulfur-containing medicaments (sufa drugs) such as sulfamethazine, sulfathiazole and the like; growth stimulants such as Monesin® sodium and Elfazepam®; antiflea agents (defleaing agents) such as dexamethazone and flumethazone; agents influencing digestion in the rumen and ionophores, such as lasalocid, virginamiycin, salinomycin and ronnel; minerals such as copper oxide, cobalt sulfate, potassium iodate, zinc oxide, manganese sulfate, zinc sulfate, selenium, sodium selenite, beneficial mineral salts and the like; antibloating agents such as organic polysiloxanes; hormonal growth additions such as stilbestrol; vitamins such as vitamins A and D; with 500 000:100 100 IU/f, vitamin E with 500 000 IU/f and the like; antienteritis agents such as furazolidone, growth factors, nutrient additions such as lysine monohydrochloride, methionine, magnesium carbonate and the like; β agonists, elenbuterol and the like, and chemical markers such as chromium oxide, and salts of ytterbium and erbium.

The locally acting active ingredients further include fungicides such as amphotericin B, antibiotics such as penicillins, cephalosporins, erythromycin, tetracycline, aminoglycosides, antiviral compounds such as acyclovir, idoxuridine, breath improvers such as chlorophyll, tissue growth-inhibiting compounds, anticaries compounds such as metal fluorides, especially sodium monofluorophosphate, tin fluoride, amine fluoride, analgesics such as methyl salicylate, local anesthetics such as benzocaine, oral antiseptics such as chlorhexidine and its salts, hexylresorcinol, dequalinium chloride, cetylpyridine chloride), antiinflammatory agents, hormones such as estriol, antiplaque compounds such as chlorhexidine and its salts, octenidine, or mixtures of thymol, menthol, methyl salicylate, eucalyptol, buffer compounds such as potassium phosphate, calcium carbonate, sodium bicarbonate, sodium hydroxide and potassium hydroxide, and desensitizers for teeth such as, for example, potassium nitrate.

Further suitable active active ingredients are disinfectants such as chlorine compounds, especially calcium hypochlorite, an insecticide, pesticide, herbicide, fungicide, or growth promoters or fertilizers such as, for example, nitrogen-containing compounds, especially urea, urea-formaldehyde compounds, calium nitrate, calium sulfate, calium chloride, ammonium nitrate, ammonium sulfate, monoammonium phosphate, dibasic ammonium phosphate, ammonium-phosphoric acid compounds, trace elements for food products such as iron, zinc, manganese, copper, boron, molybdenum or mixtures thereof.

Active ingredients suitable for the inventive dosage form are also steroid hormones such as:

progestationally active steroid hormones such as, for example, 13-ethyl-17β-hydroxy-18,19-dinor-17α-pregn-4-en-20yl-3-one, 13-ethyl-17β-hydroxy-18,19-dinor-17α-pregna-4,15-dien-20yn-3-one (=gestodene), 13-ethyl-17β-hydroxy-11-methylene-18,19-dinor-17α-pregn-4-en-20yne or 13-ethyl-11-methylene-17β-hydroxy-18,19-dinor-17α-pregn-4-en-3-one (3-keto-desogestrel), estrogenically active steroid hormones 3-hydroxy-1,3,5-(10)-estratrien-17-one (=estrone), 1,3,5(10)-estratriene-3,17β-diol or 1,9-nor-17α-pregna-1,3,5(10)-trien-20yne-3,17β-diol, 17β-hydroxy-19-nor-17α-pregn-4-en-20yn-3-one, 14α17α-ethano-1,3,5-(10)-estratriene-3,17β-diol (=cyclodiol) and 14α,17α-ethano-1,3,5-(10)-estratriene-3,16α,17β-triol (=cyclotriol) and combinations of these progestins and estrogens.

Androgenically active steroid hormones such as 17β-(hydroxy-4-androsten-3-one (=testosterone) and its esters or 17β-hydroxy-1α-methyl-5α-androsten-3-one (=mesterolone).

Antiandrogenically active steroid hormones such as 17α-acetoxy-6-chloro-1β,2β- dihydro-3H-cyclopropa[1,2]-pregna-1,4,6-triene-3,20-dione.

Corticoids such as 11β,17α,21-trihydroxy-4-pregnene-3,20-dione, 11β,17α,21-trihydroxy-1,4-pegnadiene-3,20-dione, 11β,17α,21-trihydroxy-6α-methyl-1,4-pregna-triene-3,20-dione and 6α-fluoro-11β,21-dihydroxy-16α-methyl-1,4-pregnadiene-3,20-dione (=diflucortolone) and esters thereof.

Further suitable active ingredients are:

ergoline derivatives such as lisuride, [3-(9,10-didehydro-6-methyl-8α-ergolinyl)-1,1-diethylurea], bromolisuride [=3-(2-bromo-9,10-dehydro-6-methyl-8α-ergolinyl-1,1-diethylurea], terguride [=3-(6-methyl-8α-ergolinyl-1,1-diethylurea] and proterguride [=3-(6-propyl-8α-ergolinyl)-1,1-diethylurea].

Antihypertensives such as 7α-acetylthio-17α-hydroxy-3-oxo-4-pregnene-21-carboxylic acid γ-lactone and 7α-acetylthio-15β,16β-methylene-3-oxo-17α-pregna-1,4-diene-21,17-carbolactone (=mespirenone).

Anticoagulants such as 5-[hexahydro-5-hydroxy-4-(3-hydroxy-4-methyl-1-octen-6-ynyl)-2(1H)-pentalenyl-idene)]pentanoic acid (=iloprost) or (Z)-7-[(1R,2R,3R,5R)-5-chloro-2-hydroxy-2-[(E)-(3R)-3-hydroxy-4,4-dimethyl-1-octenyl]cyclopentyl]-5-heptenoic acid (=nocloprost).

Psychoactive drugs such as 4-(3-cyclopentyloxy-4-methoxyphenyl-2-pyrrolidone (=rolipram) and 7-chloro-1,3-dihydro-1-methyl-5-phenyl-2H-1,4-benzo-diazepin-2-one.

The active ingredient-containing and/or nutrient-containing layer of the inventive dosage form is preferably produced by in situ crosslinking with polyacrylic acid derivatives during formation of the layer. A suitable weight ratio of hydrophilic polymers to polyacrylic acid derivative(s) is from 5:1 to 5:4, and a particularly suitable weight ratio is from 5:2 to 5:3.

The inventive dosage forms in film form may have multiple layers. If the dosage forms in film form have multiple layers, they may have more than one active ingredient-containing and/or nutrient-containing layer, a covering layer and where appropriate an adhesive layer.

The active ingredient-containing and/or nutrient-containing layer(s) in the inventive dosage form in film form is/are based on hydrophilic polymers crosslinked with polyacrylic acid derivatives. The active ingredient-containing and/or nutrient-containing layer(s) may comprise the active ingredient in a molecular and/or particulate form.

The release of active ingredient and/or nutrient from the active ingredient-containing and/or nutrient-containing layer or the further active ingredient-containing and/or nutrient-containing layers which are present can be controlled not only by a different active ingredient and/or nutrient concentration but also by the degree of crosslinking of the hydrophilic polymers. Within an active ingredient-containing and/or nutrient-containing layer it is possible for example to control the release by a concentration gradient of the active ingredient and/or of the nutrient. A further possibility for influencing the release of active ingredient and/or nutrient is to provide a plurality of active ingredient-containing and/or nutrient-containing layers with different active ingredient and/or nutrient concentrations in the inventive dosage forms in film form. It is also possible moreover for active ingredient-free or nutrient-free layers, where appropriate composed of crosslinked hydrophilic polymers, to be present between the active ingredient-containing or nutrient-containing layers. It is thus possible for the active ingredient to be released rapidly and in an amount sufficient to achieve an immediate effect from a first active ingredient-containing layer based on hydrophilic polymers, while a longer-lasting release of active ingredient is made possible from further active ingredient-containing layers to achieve a prolonged effect.

The active ingredient-containing and/or nutrient-containing layer preferably has a thickness of 30-500 µm.

The inventive dosage form in film form preferably has a covering layer. The covering layer preferably consists of a water-insoluble polymer and is impermeable for the active ingredient and/or nutrient. This ensures unidirectional release of active ingredient and/or nutrient. With this unidirectional release, the active ingredient and/or nutrient is released only at the site of application.

The covering layer consists of at least one water-insoluble cellulose ether, preferably of alkylcellulose, particularly preferably of ethylcellulose, or of a water-insoluble cellulose ester, preferably cellulose acetate, and/or of a water-insoluble poly(meth)acrylate, preferably a poly(C1-4)-alkyl (meth) acrylate, poly(C1-4)dialkylamino-(C1-4)alkyl(meth)acrylate and/or copolymers thereof, very particularly preferably a copolymer of ethyl acrylate/methyl methacrylate and/or a copolymer of ethyl acrylate/methyl methacrylate/trimethylammonium-methyl methacrylate chloride. A covering layer may, where appropriate, comprise plasticizers in addition to cellulose ethers, cellulose esters and/or poly(meth)-acrylates.

In a preferred embodiment of the claimed invention, the covering layer is composed of ethylcellulose or of a copolymer of ethyl acrylate/methyl methacrylate/-trimethylammoniumethyl methacrylate chloride with a molar ratio of the respective monomers of 1:2:0.1, in both cases with a percentage amount of plasticizer, preferably triethyl citrates, of from 20 to 40% by weight based on the amount of polymer. A very particularly preferred covering layer consists of a copolymer of ethyl acrylate/methyl methacrylate with a molar ratio of the respective monomers of 2:1 (plasticizer addition not absolutely necessary in this case).

The covering layer preferably has a thickness of from 10 to 100 µm.

In order to ensure better adhesion of the inventive dosage form on transmucosal or transdermal administration, it is possible to provide an additional layer as adhesive layer in the inventive dosage form, which consists exclusively of polyacrylic acid derivatives, for example of an optionally crosslinked polyacrylic acid, preferably of a polyacrylic acid crosslinked with allylsucrose or allylpentaerythritol (carbomer according to USP-NF) and/or a polyacrylic acid crosslinked with divinyl glycol, where appropriate neutralized with calcium (polycarbophil according to USP-NF). A polyacrylic acid crosslinked with divinylglycol is particularly preferred in this case.

The adhesive layer preferably has a thickness of from 10 to 100 μm.

However, use of the crosslinker of polyacrylic acid derivatives is normally sufficient to achieve an adequate adhesion of the active ingredient-containing layer.

The inventive dosage form in film form can be covered with a protective layer before application.

The inventive dosage form in film form is produced by forming the active ingredient-containing and/or nutrient-containing layer or the active ingredient-containing and/or nutrient-containing layers, preferably from an aqueous solution of the hydrophilic polymers and of the active ingredient and/or of the nutrient by application with simultaneous or subsequent exposure to the polyacrylic acid derivative as crosslinker, preferably as aqueous solution, and removal of the water by drying. The covering layer can be produced by applying to the dried active ingredient-containing and/or nutrient-containing layer an aqueous dispersion such as a latex or pseudolatex dispersion of a water-insoluble polymer or a solution of such a polymer in a suitable organic solvent with subsequent removal of the water or organic solvent by drying and/or vacuum treatment.

If an adhesive layer is present on the inventive dosage form in film form, this is preferably composed of an aqueous solution or dispersion of optionally crosslinked polyacrylic acids.

The inventive dosage form in film form is preferably produced by building up the individual layers successively on a smooth surface, applying the film-forming polymer in each case together with the crosslinker which is optionally present and with the active ingredient and/or nutrient which is optionally present on each layer by spraying and drying as sub-layers. The drying in this case preferably takes place simultaneously with the spraying. The sub-layers preferably have a thickness of from 0.1 to 10 μm.

The spraying of the aqueous solution of hydrophilic polymers and of the aqueous solution of the crosslinker preferably takes place simultaneously, in which case the hydrophilic polymers and the crosslinker mix after the spraying and the polymer is then crosslinked in situ.

If the active ingredient and/or nutrient is present in one layer, the loading preferably takes place through the active ingredient and/or nutrient already being dissolved in the aqueous solution of hydrophilic polymers before this solution is brought together with the solution of the crosslinker.

The great variability of this procedure permits the layers to be built up in any sequence. It is thus possible to form first the adhesive layer, if present, or first the covering layer as basis for the subsequent layers.

The production process is preferably carried out employing an apparatus as described in DE 101 46 251. The corresponding disclosure is incorporated in the present disclosure.

This device comprises at least one spraying device, a dryer and at least one plate which is moved cyclically underneath the spraying device. The device preferably has a plurality of nozzles whose spray cones overlap.

Method for Determining the Tear Strength

A TA.XT2i texture analyzer from Winopal (Germany) is employed to determine the tear strength. Pieces of the active ingredient-containing and/or nutrient-containing layer film with a length of 9.5 cm and a width of 1 cm are clamped at both ends with clamping jaws and slightly stretched so that the free tension length is 7 cm. The clamping jaws are provided with coatings on the surface which come into contact with the pieces in order to avoid premature tearing of the pieces at the clamps. If a piece tears, despite the coatings on the clamps, these values are not taken into account. The upper clamp pulls upwards at a constant speed of 0.5 mm/s. The force employed at every time during this, and the resulting extension, is recorded by the texture analyzer. The force, the extension and the time are then displayed and analyzed with the aid of software.

The tear strength of an investigated piece of film is the force acting on the piece of film just at the moment when the particular piece tears.

EXAMPLES

Example 1 a) To produce the active ingredient-containing layer, a solution of 10 g of hydroxypropylmethylcellulose, 1 g of the active ingredient prednisolone and 489 g of water, a solution of 2 g of polycarbophil in acidic form in 498 g of water was prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness of the active ingredient-containing layer reached 200 μm.

b) To produce the covering layer, a 10% strength aqueous latex of an ethylacryl/methyl methacrylate copolymer with a 2:1 molar ratio of the monomers, obtained by diluting 333.33 g of a 30% strength aqueous latex with 666.67 g of water, with the aid of the apparatus described in DE 101 46 251 in a multiple spraying process in which the sublayers were produced each time, until the layer thickness of the covering layer reached 50 μm.

The dosage form produced in this way was easy to handle and easy to apply to the human skin and to human mucous membranes, for example to the buccal mucosa.

Example 2

A dosage form was produced in the same manner as described in Example 1, with the difference that an adhesive layer was applied before the active ingredient-containing layer by spraying on a solution of 6 g of polyacrylic acid crosslinked with divinylglycol (Polycarbophil®) in 494 g of water until the layer thickness reached 50 μm.

The dosage form produced in this way was easy to handle and easy to apply to the human skin and to human mucous membranes, for example to the buccal mucosa.

Example 3

A dosage form was produced in the same manner as described in Example 1, with the difference that 4 g, instead of 2 g, of polycarbophil, and correspondingly 496 g of water, were employed.

The dosage form produced in this way was easy to handle and easy to apply to the human skin and to human mucous membranes, for example to the buccal mucosa.

Example 4

A dosage form was produced in the same manner as described in Example 1, with the difference that 6 g, instead of 2 g, of polycarbophil, and correspondingly 494 g of water, were employed.

The dosage form produced in this way was easy to handle and easy to apply to the human skin and to human mucous membranes, for example to the buccal mucosa.

All the active ingredient-containing layers of Examples 1 to 4 showed in each case a tear strength exceeding 40 N as determined by the method indicated above.

Example 5

A dosage form was produced in the same manner as described in Example 1, with the difference that 8 g, instead of 2 g, of polycarbophil, and correspondingly 492 g of water, were employed.

The dosage form produced in this way was easy to handle and easy to apply to the human skin and to human mucous membranes, for example to the buccal mucosa.

Example 6

To produce an active ingredient-free layer whose color and taste was to be investigated, a solution of 10 g of hydroxypropylmethylcellulose and 490 g of water, and a solution of 2.5 g of polycarbophil in acidic form in 498 g of water was prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness of the active ingredient-containing layer reached 200 μm.

The active ingredient-free layer produced in this way has neither a yellowish color nor an unpleasant taste.

Comparative Example 1

To produce an active ingredient-free layer whose color and taste was to be investigated, a solution of 10 g of hydroxypropylmethylcellulose and 490 g of water, and a solution of 2.5 g of tannin in 498 g of water was prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness of the active ingredient-containing layer reached 200 μm.

The active ingredient-free layer produced in this way has a yellowish color and an unpleasant taste.

The invention claimed is:

1. A process for producing a dosage form in film form for surface administration of at least one active ingredient and/or nutrient to a living creature comprising at least one active ingredient-containing and/or nutrient-containing layer based on hydrophilic polymers crosslinked with at least one polyacrylic acid derivative by building up individual layers successively on a smooth surface, characterized by the steps:
   a) simultaneous spraying of (1) an aqueous solution of the hydrophilic polymers and of the active ingredient and/or of the nutrient and (2) of an aqueous solution of the polyacrylic acid derivative, wherein the aqueous solution of the hydrophilic polymers and of the active ingredient and/or of the nutrient and aqueous solution of polyacrylic acid derivative are mixed after spraying and the hydrophilic polymers are crosslinked by the polyacrylic acid derivative in situ; and
   b) removal of the water by drying.

2. The production process as claimed in claim 1, characterized in that hydroxypropylmethylcellulose, hydroxyethylcellulose and/or methylcellulose, is employed as hydrophilic polymer.

3. The production process as claimed in claim 1, characterized in that the weight ratio of hydrophilic polymers to polyacrylic acid derivative(s) is from 5:1 to 5:4, 4. The production process as claimed in claim 1, characterized in that hydroxypropylmethylcellulose is employed as hydrophilic polymer.

5. The production process as claimed in claim 4, characterized in that the weight ratio of hydrophilic polymers to polyacrylic acid derivative(s) is from 5:2 to 5:3.

6. The production process as claimed in claim 5, characterized in that the dosage form has a tear strength greater than 40 N.

7. A transdermal dosage film form form produced as claimed in claim 1.

8. The dosage form as claimed in claim 7, characterized in that it has at least one active ingredient-containing and/or nutrient-containing layer, a covering layer and where appropriate an adhesive layer.

9. The dosage form as claimed in claim 7, characterized in that at least one active ingredient-containing layer has a concentration gradient of the active ingredient.

10. The dosage form as claimed in claim 7, characterized in that the covering layer is impermeable for the active ingredient and/or nutrient.

11. The dosage form as claimed in claim 7, characterized in that the dosage form is covered with a protective layer before application.

12. The dosage form as claimed in claim 7, characterized in that the dosage form has a tear strength greater than 40 N.

* * * * *